United States Patent
Kim et al.

(10) Patent No.: US 10,467,450 B2
(45) Date of Patent: Nov. 5, 2019

(54) FAN-OUT SENSOR PACKAGE

(71) Applicant: SAMSUNG ELECTRO-MECHANICS CO., LTD., Suwon-Si, Gyeonggi-Do (KR)

(72) Inventors: Ju Ho Kim, Suwon-Si (KR); Eun Sil Kim, Suwon-Si (KR); Sang Kyu Lee, Suwon-Si (KR); Jong Man Kim, Suwon-Si (KR); Seok Hwan Kim, Suwon-Si (KR)

(73) Assignee: SAMSUNG ELECTRO-MECHANICS CO., LTD., Suwon-si, Gyeonggi-Do (KR)

( * ) Notice: Subject to any disclaimer, the term of this patent is extended or adjusted under 35 U.S.C. 154(b) by 15 days.

(21) Appl. No.: 15/966,621

(22) Filed: Apr. 30, 2018

(65) Prior Publication Data
US 2019/0163945 A1    May 30, 2019

(30) Foreign Application Priority Data
Nov. 28, 2017   (KR) .......................... 10-2017-0160576

(51) Int. Cl.
*G01R 27/26*   (2006.01)
*G06K 9/00*    (2006.01)
(Continued)

(52) U.S. Cl.
CPC .............. *G06K 9/0002* (2013.01); *G01D 5/24* (2013.01); *G01N 27/22* (2013.01);
(Continued)

(58) Field of Classification Search
CPC ....... G06K 9/0002; G01N 27/22; G06F 9/223
See application file for complete search history.

(56) References Cited

U.S. PATENT DOCUMENTS

| | | | |
|---|---|---|---|
| 9,406,580 B2 | 8/2016 | Erhart et al. | |
| 2008/0211075 A1* | 9/2008 | Yang | ................ H01L 27/14618 257/680 |

(Continued)

FOREIGN PATENT DOCUMENTS

| | | |
|---|---|---|
| CN | 103779319 A | 5/2014 |
| KR | 101067109 B1 | 9/2011 |

(Continued)

OTHER PUBLICATIONS

Taiwanese Office Action dated Nov. 27, 2018 issued in Taiwanese Patent Application No. 107115153 (with English translation).
Office Action issued in corresponding Korean Patent Application No. 10-2017-0160576, dated Jun. 21, 2018.

*Primary Examiner* — Giovanni Astacio-Oquendo
*Assistant Examiner* — Alvaro E Fortich
(74) *Attorney, Agent, or Firm* — Morgan, Lewis & Bockius LLP

(57) ABSTRACT

A fan-out sensor package includes: a core member including a wiring layer including a plurality of layers and having a through-hole; an integrated circuit (IC) for a sensor disposed in the through-hole; an encapsulant encapsulating at least portions of the core member and the IC for a sensor; and a connection member disposed on the core member and the IC for a sensor and including a plurality of circuit layers, wherein the circuit layer includes sensing patterns detecting a change in capacitance.

22 Claims, 10 Drawing Sheets

(51) Int. Cl.
*G01D 5/24* (2006.01)
*G06F 9/22* (2006.01)
*G01N 27/22* (2006.01)

(52) U.S. Cl.
CPC ......... *G01R 27/2605* (2013.01); *G06F 9/223* (2013.01); *G06K 9/00053* (2013.01); *H01L 2224/18* (2013.01)

(56) References Cited

U.S. PATENT DOCUMENTS

| | | |
|---|---|---|
| 2011/0259630 A1 | 10/2011 | Park |
| 2014/0103527 A1 | 4/2014 | Marimuthu et al. |
| 2014/0110840 A1 | 4/2014 | Wojnowski et al. |
| 2015/0102829 A1 | 4/2015 | Son et al. |
| 2016/0043047 A1 | 2/2016 | Shim et al. |
| 2016/0322330 A1* | 11/2016 | Lin ................... H01L 25/0652 |
| 2016/0338202 A1 | 11/2016 | Park et al. |
| 2017/0228529 A1 | 8/2017 | Huang et al. |
| 2017/0278766 A1* | 9/2017 | Kim ................... H01L 24/20 |

FOREIGN PATENT DOCUMENTS

| | | |
|---|---|---|
| KR | 10-1356143 B1 | 1/2014 |
| KR | 10-2015-0095473 A | 8/2015 |
| KR | 10-2016-0132763 A | 11/2016 |
| TW | 201618196 A | 5/2016 |
| TW | 201729139 A | 8/2017 |

* cited by examiner

FAN-OUT SENSOR PACKAGE

CROSS-REFERENCE TO RELATED APPLICATION(S)

This application claims benefit of priority to Korean Patent Application No. 10-2017-0160576 filed on Nov. 28, 2017 in the Korean Intellectual Property Office, the disclosure of which is incorporated herein by reference in its entirety.

TECHNICAL FIELD

The present disclosure relates to a sensor package, and more particularly, to a fan-out sensor package having a fingerprint recognition function.

BACKGROUND

A printed circuit board (PCB) having a multilayer structure is generally used in a capacitive fingerprint sensor module. In general, an upper circuit layer of the printed circuit board touched by a fingerprint has a sensing pattern, and a lower circuit layer of the printed circuit board opposing the upper circuit layer has a circuit pattern on which an integrated circuit (IC), a passive component, solder balls, and the like, are mounted. In such a capacitive fingerprint sensor module, the IC and the passive component are mounted in a region in which the solder balls are mounted, on a lower surface of the printed circuit board, by surface mounting technology (SMT).

Meanwhile, the capacitive fingerprint sensor module having the structure described above is connected to a mainboard of an electronic device using the solder balls, and a sufficient height of the solder balls after being mounted (that is, a height of the solder balls higher than those of the IC and the passive component) thus needs to be secured.

SUMMARY

An aspect of the present disclosure may provide a subminiature and ultra-thin fan-out sensor package having an excellent fingerprint recognition function, a high degree of integration, and excellent rigidity.

According to an aspect of the present disclosure, a fan-out sensor package may be provided, in which a core member having a through-hole and including a plurality of wiring layers is introduced to a region in which an integrated circuit (IC) for a sensor is disposed, the IC for a sensor is disposed in the through-hole of the core member, the core member and the IC for a sensor are encapsulated, and a connection member including circuit layers capable of implementing a high sensitivity fingerprint recognition function is directly formed on the core member and the IC for a sensor. In this case, a passive component may be disposed together with the IC for a sensor in the through-hole, and the plurality of wiring layers may have different thicknesses.

According to an aspect of the present disclosure, a fan-out sensor package may include: a core member including a wiring layer including a plurality of layers and having a through-hole; an IC for a sensor disposed in the through-hole and having an active surface having connection pads disposed thereon and an inactive surface opposing the active surface; a passive component disposed side-by-side with the IC for a sensor in the through-hole and having external electrodes; an encapsulant covering at least portions of the core member, the inactive surface of the IC for a sensor, and the passive component and filling at least portions of the through-hole; and a connection member disposed on the core member, the active surface of the IC for a sensor, and the passive component and including a circuit layer including a plurality of layers, wherein the circuit layer is electrically connected to the wiring layer, the connection pads, and the external electrodes, and the circuit layer includes sensing patterns detecting a change in capacitance.

According to another aspect of the present disclosure, a fan-out sensor package may include: a core member including an insulating layer, a first wiring layer disposed on an upper surface of the insulating layer, a second wiring layer disposed on a lower surface of the insulating layer, and vias penetrating through the insulating layer and electrically connecting the first and second wiring layers to each other and having a through-hole; an IC for a sensor disposed in the through-hole; an encapsulant covering at least portions of the core member and a lower surface of the IC for sensor and filling at least portions of the through-hole; and a connection member disposed on the core member and an upper surface of the IC for a sensor and including a circuit layer including a plurality of layers, wherein the second wiring layer has a thickness greater than that of the first wiring layer.

BRIEF DESCRIPTION OF DRAWINGS

The above and other aspects, features, and advantages of the present disclosure will be more clearly understood from the following detailed description taken in conjunction with the accompanying drawings, in which.

DETAILED DESCRIPTION

Hereinafter, exemplary embodiments in the present disclosure will be described with reference to the accompanying drawings. In the accompanying drawings, shapes, sizes, and the like, of components may be exaggerated or shortened for clarity.

The meaning of a "connection" of a component to another component in the description includes an indirect connection through an adhesive layer as well as a direct connection between two components. In addition, "electrically connected" conceptually includes a physical connection and a physical disconnection. It can be understood that when an element is referred to with terms such as "first" and "second", the element is not limited thereby. They may be used only for a purpose of distinguishing the element from the other elements, and may not limit the sequence or importance of the elements. In some cases, a first element may be referred to as a second element without departing from the scope of the claims set forth herein. Similarly, a second element may also be referred to as a first element.

The term "an exemplary embodiment" used herein does not refer to the same exemplary embodiment, and is provided to emphasize a particular feature or characteristic different from that of another exemplary embodiment. However, exemplary embodiments provided herein are considered to be able to be implemented by being combined in whole or in part one with one another. For example, one element described in a particular exemplary embodiment, even if it is not described in another exemplary embodiment, may be understood as a description related to another exemplary embodiment, unless an opposite or contradictory description is provided therein.

Terms used herein are used only in order to describe an exemplary embodiment rather than limiting the present disclosure. In this case, singular forms include plural forms unless interpreted otherwise in context.

Electronic Device

Figure 1:
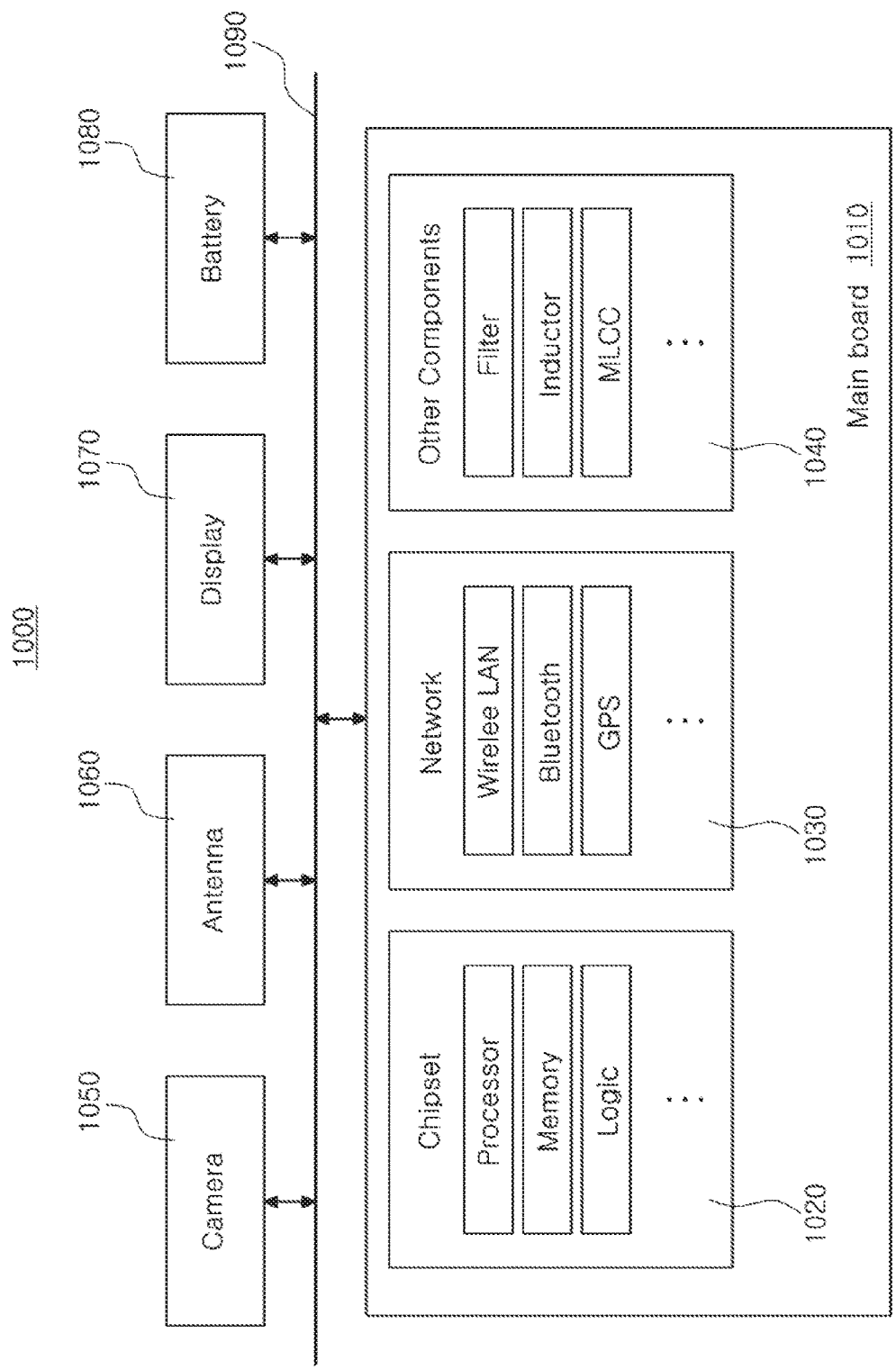
FIG. 1 is a schematic block diagram illustrating an example of an electronic device system.

FIG. 1 is a schematic block diagram illustrating an example of an electronic device system.

Referring to FIG. 1, an electronic device 1000 may accommodate a mainboard 1010 therein. The mainboard 1010 may include chip related components 1020, network related components 1030, other components 1040, and the like, physically or electrically connected thereto. These components may be connected to others to be described below to form various signal lines 1090.

The chip related components 1020 may include a memory chip such as a volatile memory (for example, a dynamic random access memory (DRAM)), a non-volatile memory (for example, a read only memory (ROM)), a flash memory, or the like; an application processor chip such as a central processor (for example, a central processing unit (CPU)), a graphics processor (for example, a graphics processing unit (GPU)), a digital signal processor, a cryptographic processor, a microprocessor, a microcontroller, or the like; and a logic chip such as an analog-to-digital (ADC) converter, an application-specific integrated circuit (ASIC), or the like. However, the chip related components 1020 are not limited thereto, but may also include other types of chip related components. In addition, the chip related components 1020 may be combined with each other.

The network related components 1030 may include protocols such as wireless fidelity (Wi-Fi) (Institute of Electrical And Electronics Engineers (IEEE) 802.11 family, or the like), worldwide interoperability for microwave access (Wi-MAX) (IEEE 802.16 family, or the like), IEEE 802.20, long term evolution (LTE), evolution data only (Ev-DO), high speed packet access+ (HSPA+), high speed downlink packet access+ (HSDPA+), high speed uplink packet access+ (HSUPA+), enhanced data GSM environment (EDGE), global system for mobile communications (GSM), global positioning system (GPS), general packet radio service (GPRS), code division multiple access (CDMA), time division multiple access (TDMA), digital enhanced cordless telecommunications (DECT), Bluetooth, 3G, 4G, and 5G protocols, and any other wireless and wired protocols, designated after the abovementioned protocols. However, the network related components 1030 are not limited thereto, but may also include a variety of other wireless or wired standards or protocols. In addition, the network related components 1030 may be combined with each other, together with the chip related components 1020 described above.

Other components 1040 may include a high frequency inductor, a ferrite inductor, a power inductor, ferrite beads, a low temperature co-fired ceramic (LTCC), an electromagnetic interference (EMI) filter, a multilayer ceramic capacitor (MLCC), or the like. However, other components 1040 are not limited thereto, but may also include passive components used for various other purposes, or the like. In addition, other components 1040 may be combined with each other, together with the chip related components 1020 or the network related components 1030 described above.

Depending on a type of the electronic device 1000, the electronic device 1000 may include other components that may or may not be physically or electrically connected to the mainboard 1010. These other components may include, for example, a camera module 1050, an antenna 1060, a display device 1070, a battery 1080, an audio codec (not illustrated), a video codec (not illustrated), a power amplifier (not illustrated), a compass (not illustrated), an accelerometer (not illustrated), a gyroscope (not illustrated), a speaker (not illustrated), a mass storage unit (for example, a hard disk drive) (not illustrated), a compact disk (CD) drive (not illustrated), a digital versatile disk (DVD) drive (not illustrated), or the like. However, these other components are not limited thereto, but may also include other components used for various purposes depending on a type of electronic device 1000, or the like.

The electronic device 1000 may be a smartphone, a personal digital assistant (PDA), a digital video camera, a digital still camera, a network system, a computer, a monitor, a tablet PC, a laptop PC, a netbook PC, a television, a video game machine, a smartwatch, an automotive component, or the like. However, the electronic device 1000 is not limited thereto, but may be any other electronic device processing data.

Figure 2:
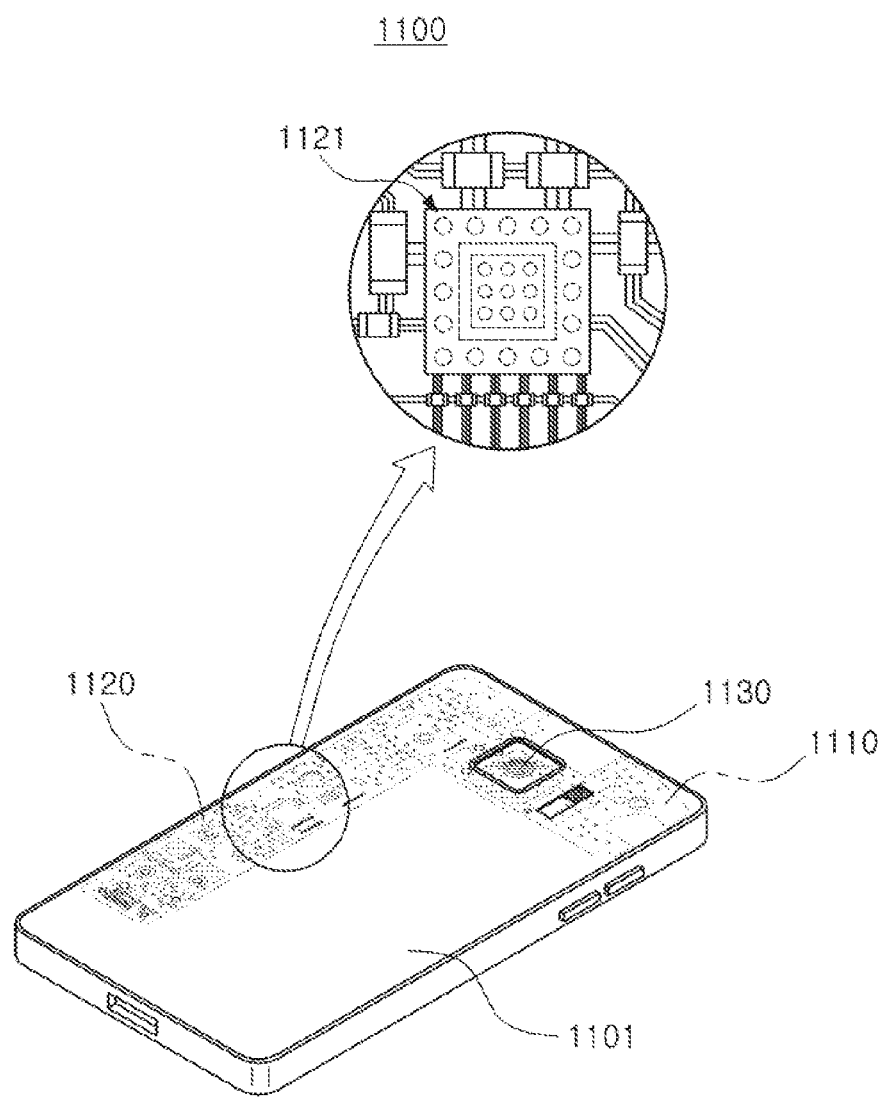
FIG. 2 is a schematic perspective view illustrating an example of an electronic device.

FIG. 2 is a schematic perspective view illustrating an example of an electronic device.

Referring to FIG. 2, a semiconductor package may be used for various purposes in the various electronic devices 1000 as described above. For example, a motherboard 1110 may be accommodated in a body 1101 of a smartphone 1100, and various electronic components 1120 may be physically or electrically connected to the motherboard 1110. In addition, other components that may or may not be physically or electrically connected to the motherboard 1110, such as a camera module 1130, may be accommodated in the body 1101. Some of the electronic components 1120 may be the chip related components, for example, a semiconductor package 1121, but are not limited thereto. The electronic device is not necessarily limited to the smartphone 1100, but may be other electronic devices as described above.

Semiconductor Package

Generally, numerous fine electrical circuits are integrated in a semiconductor chip. However, the semiconductor chip may not serve as a finished semiconductor product in itself, and may be damaged due to external physical or chemical impacts. Therefore, the semiconductor chip itself may not be used, but may be packaged and used in an electronic device, or the like, in a packaged state.

Here, semiconductor packaging is required due to the existence of a difference in a circuit width between the semiconductor chip and a mainboard of the electronic device in terms of electrical connections. In detail, a size of connection pads of the semiconductor chip and an interval between the connection pads of the semiconductor chip are very fine, but a size of component mounting pads of the mainboard used in the electronic device and an interval between the component mounting pads of the mainboard are significantly larger than those of the semiconductor chip. Therefore, it may be difficult to directly mount the semiconductor chip on the mainboard, and packaging technology for buffering a difference in a circuit width between the semiconductor chip and the mainboard is required.

A semiconductor package manufactured by the packaging technology may be classified as a fan-in semiconductor package or a fan-out semiconductor package depending on a structure and a purpose thereof.

The fan-in semiconductor package and the fan-out semiconductor package will hereinafter be described in more detail with reference to the drawings.

Fan-in Semiconductor Package

Figure 3B:
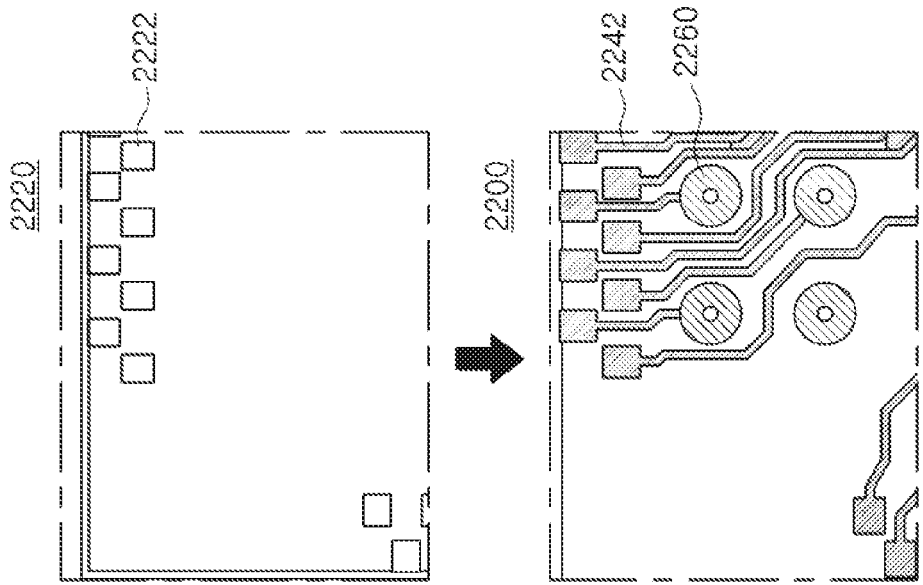
FIGS. 3A and 3B are schematic cross-sectional views illustrating states of a fan-in semiconductor package before and after being packaged.
Figure 3A:
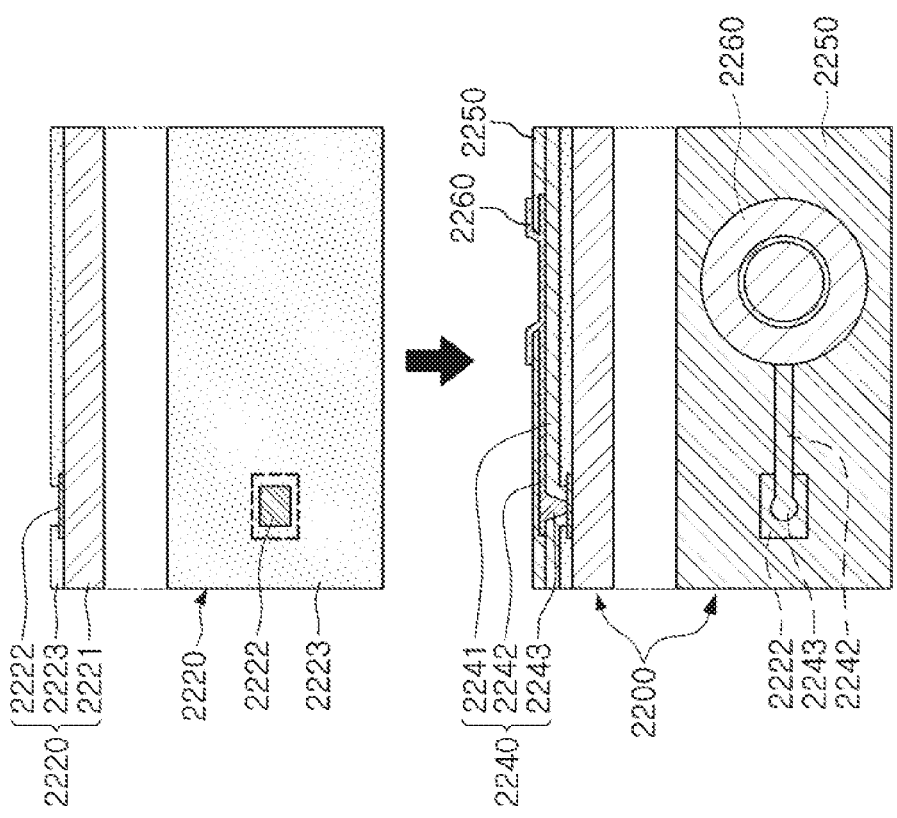

FIGS. 3A and 3B are schematic cross-sectional views illustrating states of a fan-in semiconductor package before and after being packaged.

Figure 4:
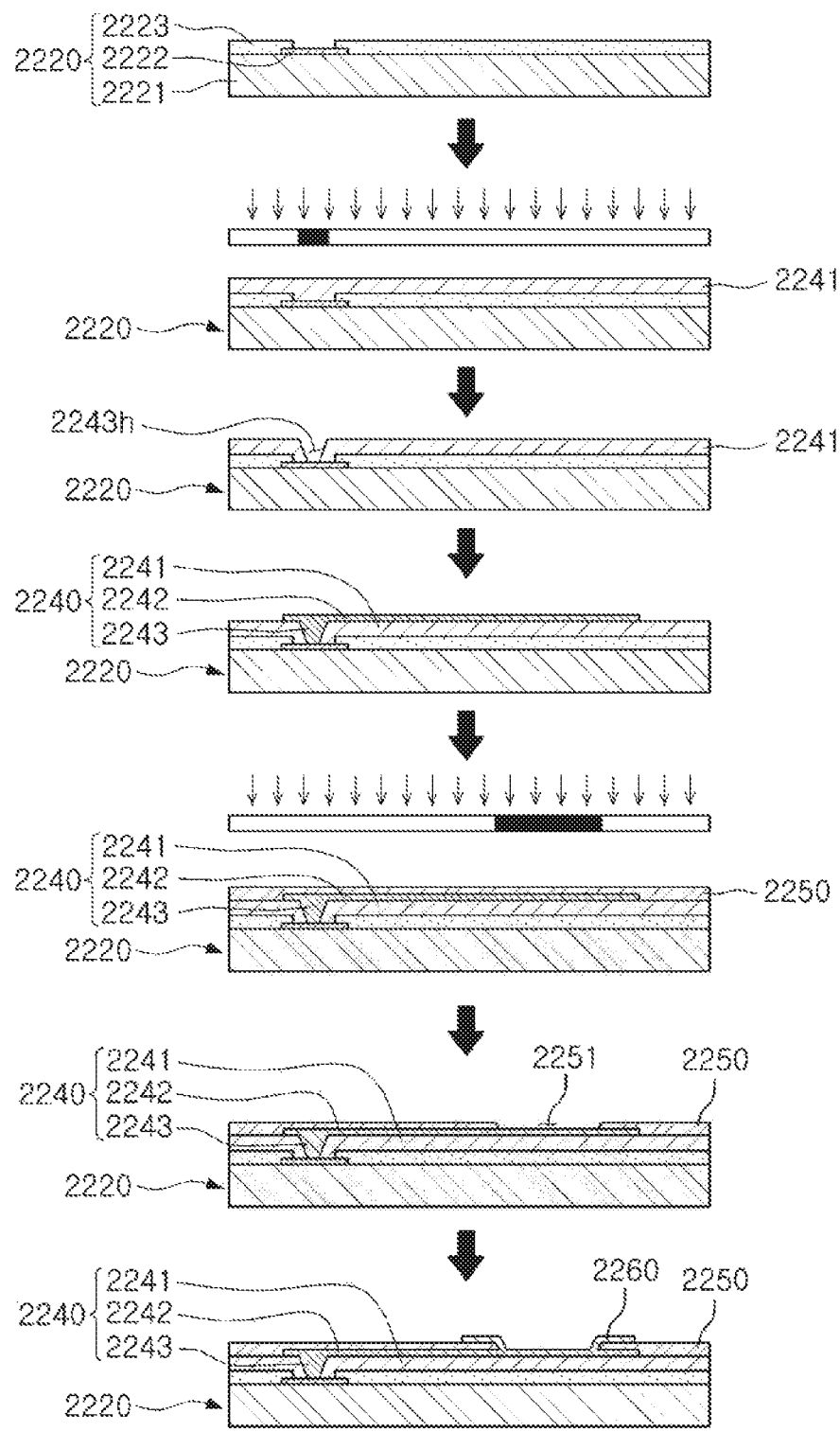
FIG. 4 is schematic cross-sectional views illustrating a packaging process of a fan-in semiconductor package.

FIG. 4 is schematic cross-sectional views illustrating a packaging process of a fan-in semiconductor package.

Referring to FIGS. 3 and 4, a semiconductor chip 2220 may be, for example, an integrated circuit (IC) in a bare state, including a body 2221 including silicon (Si), germanium (Ge), gallium arsenide (GaAs), or the like, connection pads 2222 formed on one surface of the body 2221 and including a conductive material such as aluminum (Al), or the like, and a passivation layer 2223 such as an oxide film, a nitride film, or the like, formed on one surface of the body 2221 and covering at least portions of the connection pads 2222. In this case, since the connection pads 2222 may be significantly small, it may be difficult to mount the integrated circuit (IC) on an intermediate level printed circuit board (PCB) as well as on the mainboard of the electronic device, or the like.

Therefore, a connection member 2240 may be formed depending on a size of the semiconductor chip 2220 on the semiconductor chip 2220 in order to redistribute the connection pads 2222. The connection member 2240 may be formed by forming an insulating layer 2241 on the semiconductor chip 2220 using an insulating material such as a photoimagable dielectric (PID) resin, forming via holes 2243*h* opening the connection pads 2222, and then forming wiring patterns 2242 and vias 2243. Then, a passivation layer 2250 protecting the connection member 2240 may be formed, an opening 2251 may be formed, and an underbump metal layer 2260, or the like, may be formed. That is, a fan-in semiconductor package 2200 including, for example, the semiconductor chip 2220, the connection member 2240, the passivation layer 2250, and the underbump metal layer 2260 may be manufactured through a series of processes.

As described above, the fan-in semiconductor package may have a package form in which all of the connection pads, for example, input/output (I/O) terminals, of the semiconductor chip are disposed inside the semiconductor chip, and may have excellent electrical characteristics and be produced at a low cost. Therefore, many elements mounted in smartphones have been manufactured in a fan-in semiconductor package form. In detail, many elements mounted in smartphones have been developed to implement a rapid signal transfer while having a compact size.

However, since all I/O terminals need to be disposed inside the semiconductor chip in the fan-in semiconductor package, the fan-in semiconductor package has significant spatial limitations. Therefore, it is difficult to apply this structure to a semiconductor chip having a large number of I/O terminals or a semiconductor chip having a compact size. In addition, due to the disadvantage described above, the fan-in semiconductor package may not be directly mounted and used on the mainboard of the electronic device. The reason is that even in a case in which a size of the I/O terminals of the semiconductor chip and an interval between the I/O terminals of the semiconductor chip are increased by a redistribution process, the size of the I/O terminals of the semiconductor chip and the interval between the I/O terminals of the semiconductor chip may not be sufficient to directly mount the fan-in semiconductor package on the mainboard of the electronic device.

Figure 5:
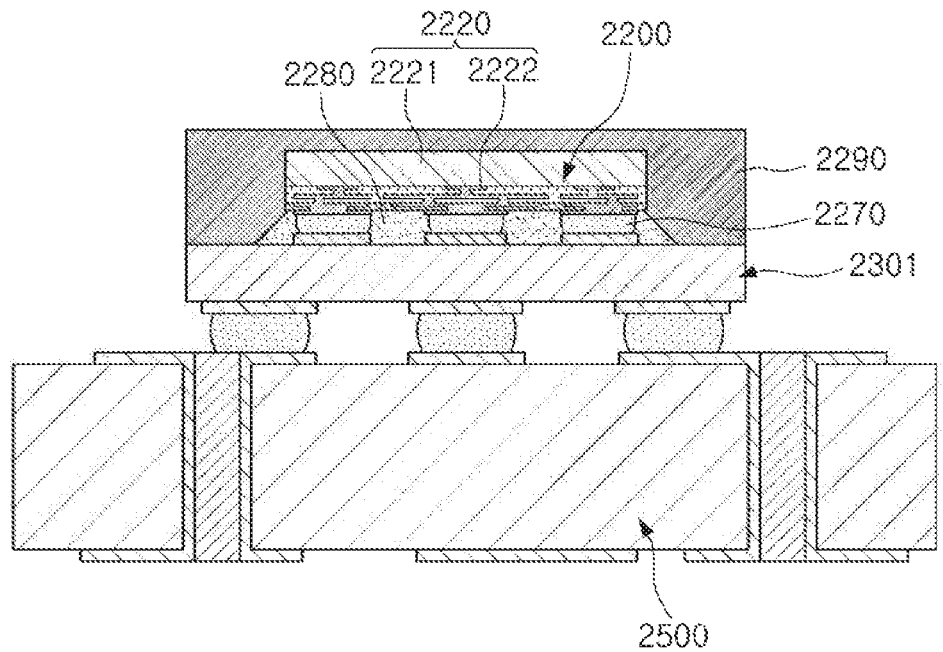
FIG. 5 is a schematic cross-sectional view illustrating a case in which a fan-in semiconductor package is mounted on a ball grid array (BGA) substrate and is ultimately mounted on a mainboard of an electronic device.

FIG. 5 is a schematic cross-sectional view illustrating a case in which a fan-in semiconductor package is mounted on a ball grid array (BGA) substrate and is ultimately mounted on a mainboard of an electronic device.

Figure 6:
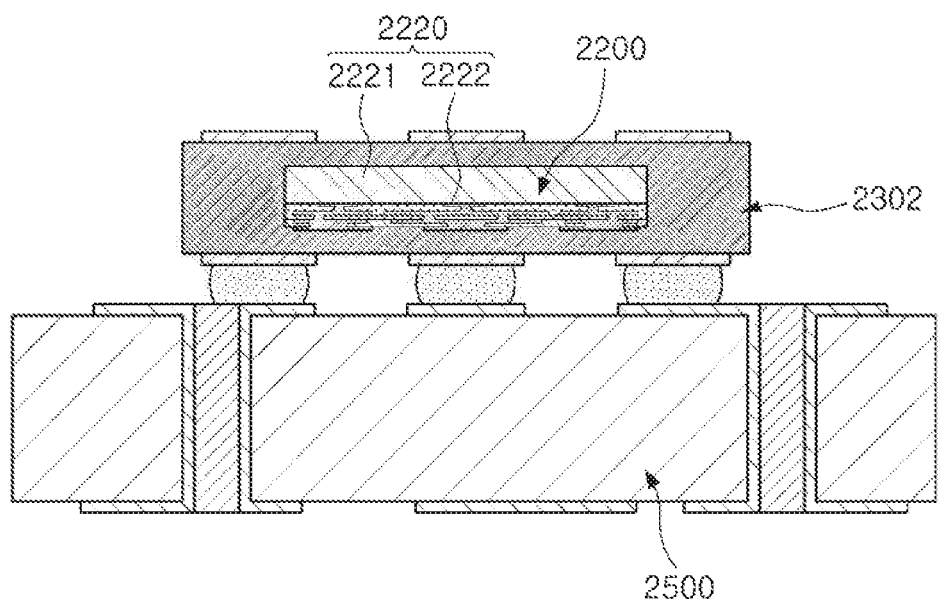
FIG. 6 is a schematic cross-sectional view illustrating a case in which a fan-in semiconductor package is embedded in a BGA substrate and is ultimately mounted on a mainboard of an electronic device.

FIG. 6 is a schematic cross-sectional view illustrating a case in which a fan-in semiconductor package is embedded in a BGA substrate and is ultimately mounted on a mainboard of an electronic device.

Referring to FIGS. 5 and 6, in a fan-in semiconductor package 2200, connection pads 2222, that is, I/O terminals, of a semiconductor chip 2220 may be redistributed through a BGA substrate 2301, and the fan-in semiconductor package 2200 may be ultimately mounted on a mainboard 2500 of an electronic device in a state in which it is mounted on the BGA substrate 2301. In this case, solder balls 2270, and the like, may be fixed by an underfill resin 2280, or the like, and an outer side of the semiconductor chip 2220 may be covered with a molding material 2290, or the like. Alternatively, a fan-in semiconductor package 2200 may be embedded in a separate BGA substrate 2302, connection pads 2222, that is, I/O terminals, of the semiconductor chip 2220 may be redistributed by the BGA substrate 2302 in a state in which the fan-in semiconductor package 2200 is embedded in the BGA substrate 2302, and the fan-in semiconductor package 2200 may be ultimately mounted on a mainboard 2500 of an electronic device.

As described above, it may be difficult to directly mount and use the fan-in semiconductor package on the mainboard of the electronic device. Therefore, the fan-in semiconductor package may be mounted on the separate BGA substrate and be then mounted on the mainboard of the electronic device through a packaging process or may be mounted and used on the mainboard of the electronic device in a state in which it is embedded in the BGA substrate.

Fan-Out Semiconductor Package

Figure 7:
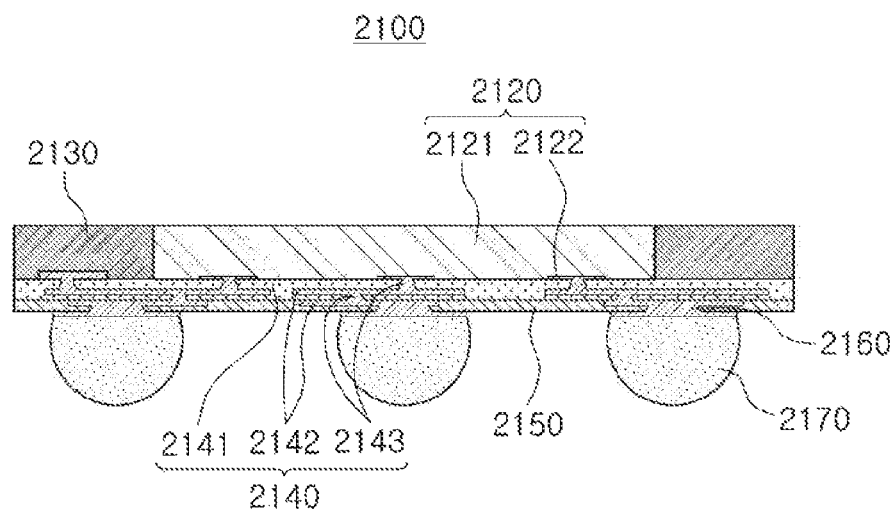
FIG. 7 is a schematic cross-sectional view illustrating a fan-out semiconductor package.

FIG. 7 is a schematic cross-sectional view illustrating a fan-out semiconductor package.

Referring to FIG. 7, in a fan-out semiconductor package 2100, for example, an outer side of a semiconductor chip 2120 may be protected by an encapsulant 2130, and connection pads 2122 of the semiconductor chip 2120 may be redistributed outwardly of the semiconductor chip 2120 by a connection member 2140. In this case, a passivation layer 2150 may further be formed on the connection member 2140, and an underbump metal layer 2160 may further be formed in openings of the passivation layer 2150. Solder balls 2170 may further be formed on the underbump metal layer 2160. The semiconductor chip 2120 may be an integrated circuit (IC) including a body 2121, the connection pads 2122, a passivation layer (not illustrated), and the like. The connection member 2140 may include an insulating layer 2141, redistribution layers 2142 formed on the insulating layer 2141, and vias 2143 electrically connecting the connection pads 2122 and the redistribution layers 2142 to each other.

As described above, the fan-out semiconductor package may have a form in which I/O terminals of the semiconductor chip are redistributed and disposed outwardly of the semiconductor chip through the connection member formed on the semiconductor chip. As described above, in the fan-in semiconductor package, all I/O terminals of the semiconductor chip need to be disposed inside the semiconductor chip. Therefore, when a size of the semiconductor chip is decreased, a size and a pitch of balls need to be decreased, such that a standardized ball layout may not be used in the fan-in semiconductor package. On the other hand, the fan-out semiconductor package has the form in which the I/O terminals of the semiconductor chip are redistributed and disposed outwardly of the semiconductor chip through the connection member formed on the semiconductor chip as described above. Therefore, even in a case in which a size of the semiconductor chip is decreased, a standardized ball layout may be used in the fan-out semiconductor package as it is, such that the fan-out semiconductor package may be mounted on the mainboard of the electronic device without using a separate BGA substrate, as described below.

Figure 8:
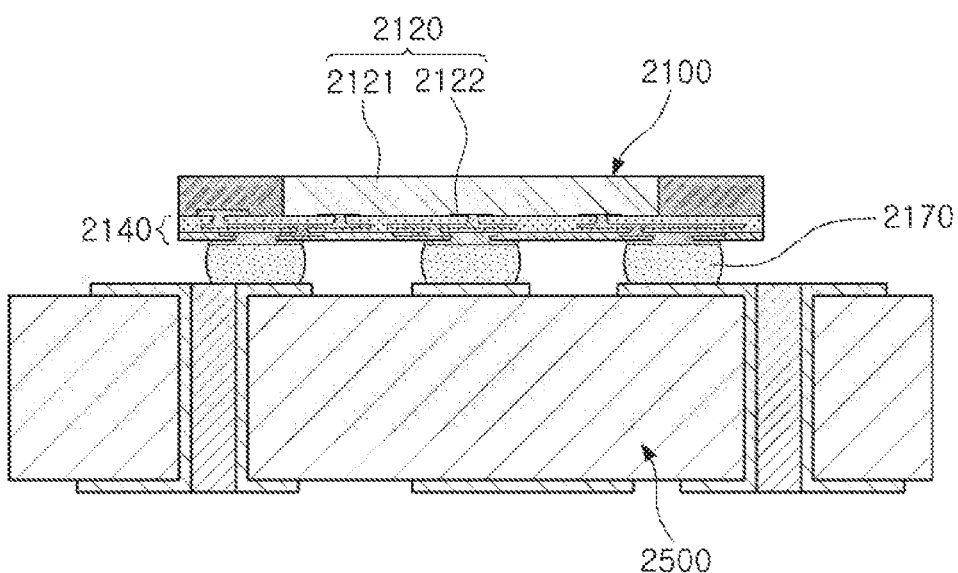
FIG. 8 is a schematic cross-sectional view illustrating a case in which a fan-out semiconductor package is mounted on a mainboard of an electronic device.

FIG. 8 is a schematic cross-sectional view illustrating a case in which a fan-out semiconductor package is mounted on a mainboard of an electronic device.

Referring to FIG. 8, a fan-out semiconductor package 2100 may be mounted on a mainboard 2500 of an electronic device through solder balls 2170, or the like. That is, as described above, the fan-out semiconductor package 2100 includes the connection member 2140 formed on the semiconductor chip 2120 and capable of redistributing the connection pads 2122 to a fan-out region that is outside of a size of the semiconductor chip 2120, such that the standardized ball layout may be used in the fan-out semiconductor package 2100 as it is. As a result, the fan-out semiconductor package 2100 may be mounted on the mainboard 2500 of the electronic device without using a separate BGA substrate, or the like.

As described above, since the fan-out semiconductor package may be mounted on the mainboard of the electronic device without using the separate BGA substrate, the fan-out semiconductor package may be implemented at a thickness lower than that of the fan-in semiconductor package using the BGA substrate. Therefore, the fan-out semiconductor package may be miniaturized and thinned. In addition, the fan-out semiconductor package has excellent thermal characteristics and electrical characteristics, such that it is particularly appropriate for a mobile product. Therefore, the fan-out semiconductor package may be implemented in a form more compact than that of a general package-on-package (POP) type using a printed circuit board (PCB), and may solve a problem due to the occurrence of a warpage phenomenon.

Meanwhile, the fan-out semiconductor package refers to package technology for mounting the semiconductor chip on the mainboard of the electronic device, or the like, as described above, and protecting the semiconductor chip from external impacts, and is a concept different from that of a printed circuit board (PCB) such as a BGA substrate, or the like, having a scale, a purpose, and the like, different from those of the fan-out semiconductor package, and having the fan-in semiconductor package embedded therein.

A subminiature and ultra-thin fan-out sensor package having an excellent fingerprint recognition function, a high degree of integration, and excellent rigidity will hereinafter be described with reference to the drawings.

Figure 9:
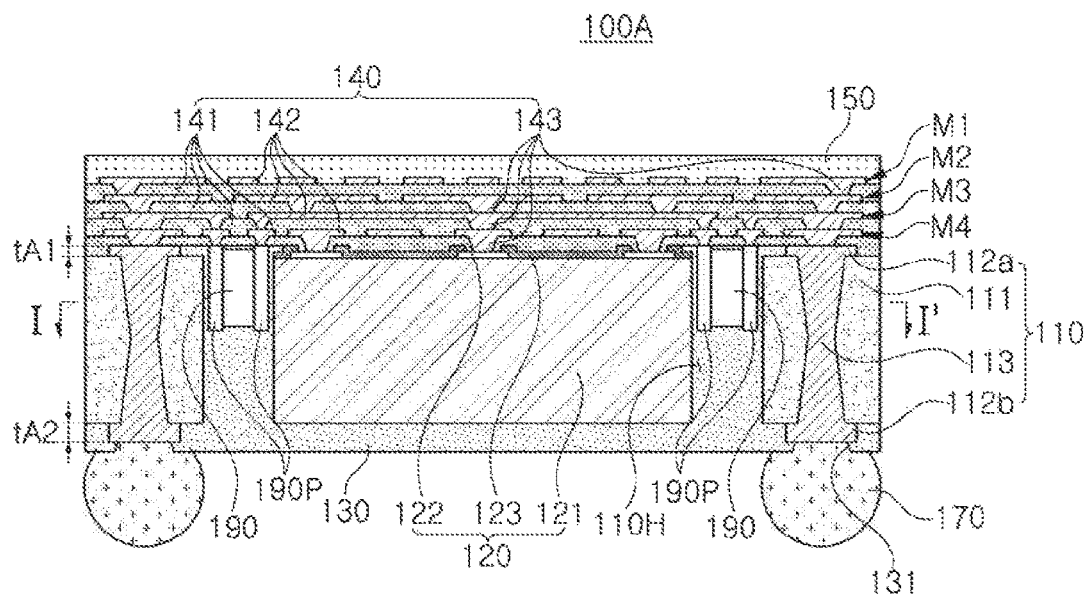
FIG. 9 is a schematic cross-sectional view illustrating an example of a fan-out semiconductor package.

FIG. 9 is a schematic cross-sectional view illustrating an example of a fan-out semiconductor package.

Figure 10:
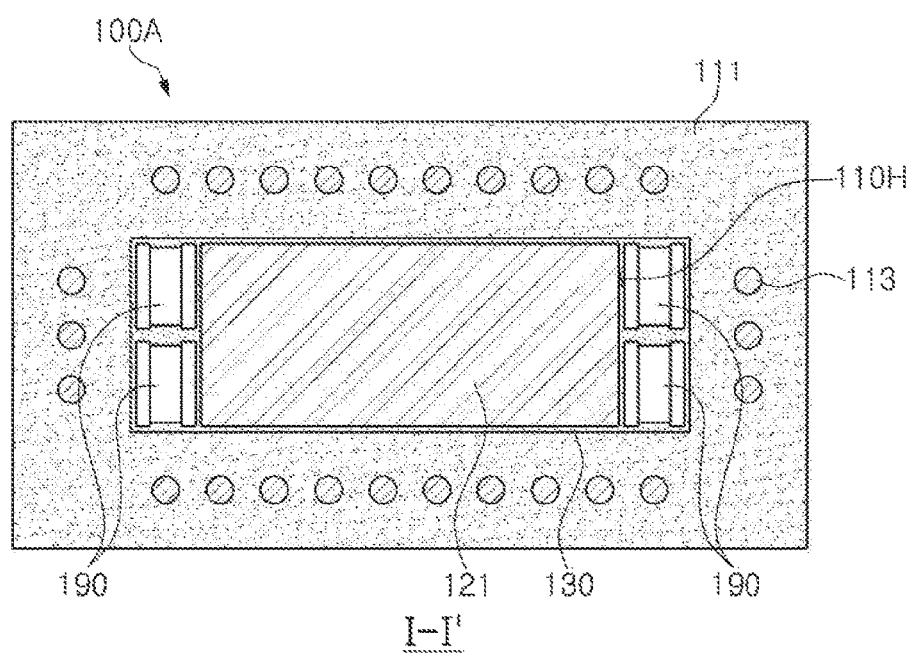
FIG. 10 is a schematic plan view taken along line I-I' of the fan-out semiconductor package of FIG. 9.

FIG. 10 is a schematic plan view taken along line I-I' of the fan-out semiconductor package of FIG. 9.

Figure 11:
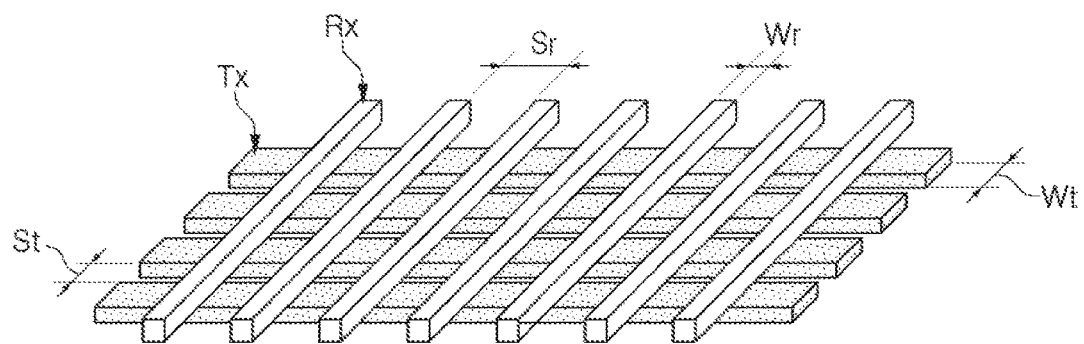
FIG. 11 is a view illustrating an example of M1 and M2 of the fan-out semiconductor package of FIG. 9.

FIG. 11 is a view illustrating an example of M1 and M2 of the fan-out semiconductor package of FIG. 9.

Figure 12:
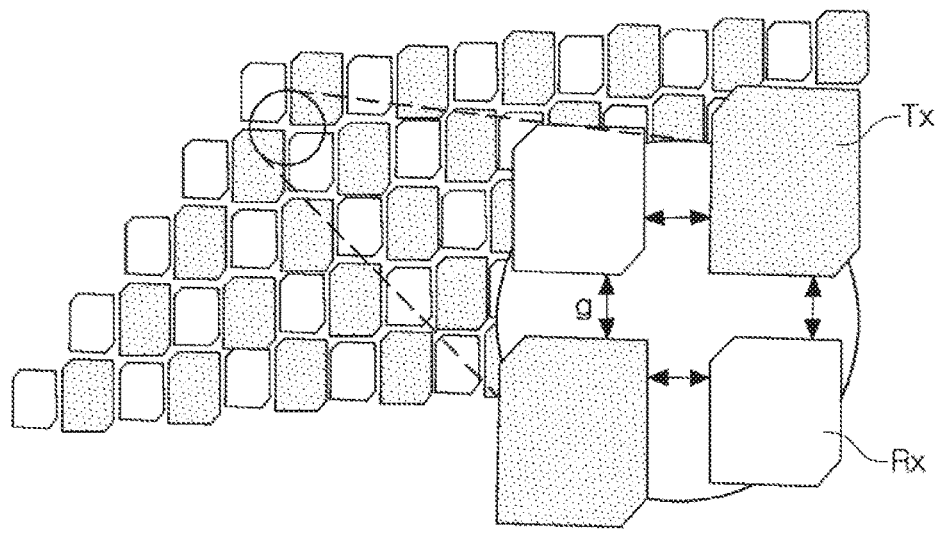
FIG. 12 is a view illustrating another example of M1 and M2 of the fan-out semiconductor package of FIG. 9.

FIG. 12 is a view illustrating another example of M1 and M2 of the fan-out semiconductor package of FIG. 9.

Figure 13:
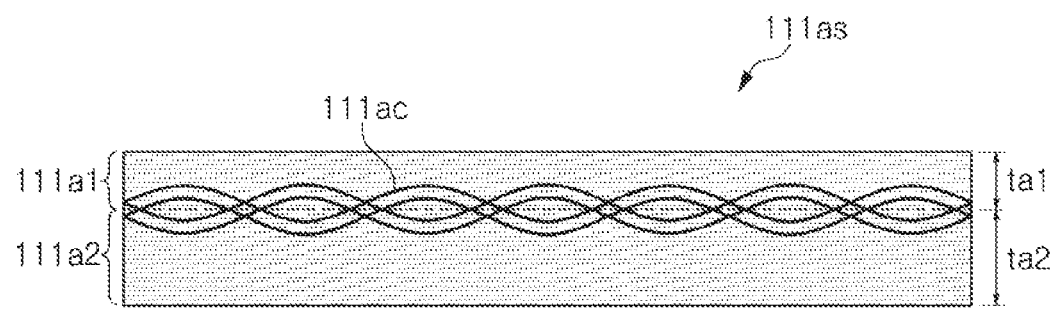
FIG. 13 is a cross-sectional view illustrating an example of an insulating layer of a core member of the fan-out semiconductor package of FIG. 9.

FIG. 13 is a cross-sectional view illustrating an example of an insulating layer of a core member of the fan-out semiconductor package of FIG. 9.

Figure 14:
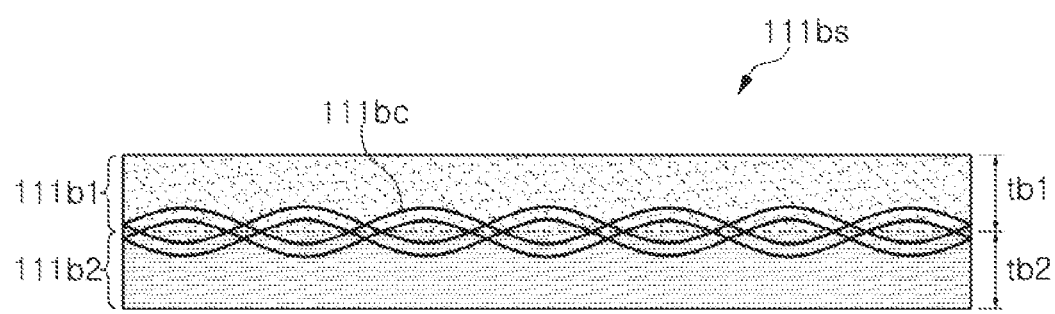
FIG. 14 is a cross-sectional view illustrating another example of an insulating layer of a core member of the fan-out semiconductor package of FIG. 9.

FIG. 14 is a cross-sectional view illustrating another example of an insulating layer of a core member of the fan-out semiconductor package of FIG. 9.

Referring to FIGS. 9 through 14, a fan-out semiconductor package 100A according to an exemplary embodiment in the present disclosure may include a core member 110 having a through-hole 110H, an integrated circuit (IC) 120 for a sensor disposed in the through-hole 110H and having an active surface having connection pads 122 disposed thereon and an inactive surface opposing the active surface, passive components 190 disposed side-by-side with the IC 120 for a sensor in the through-hole 110H and having external electrodes 190P, an encapsulant 130 covering at least portions of the core member 110, the inactive surface of the IC 120 for a sensor, and the passive components 190 and filling at least portions of the through-hole 110H, and a connection member 140 disposed on the core member 110, the active surface of the IC 120 for a sensor, and the passive components 190. The core member 110 may include a plurality of wiring layers 112a and 112b. The connection member 140 may include a plurality of circuit layers 142 electrically connected to the plurality of wiring layers 112a and 112b, the connection pads 122, and the external electrodes 190P. Circuit layers M1 and M2 disposed at an upper side of the connection member 140 among the plurality of circuit layers 142 of the connection member 140 may include sensing patterns (receive (Rx) patterns and transmit (Tx) patterns) precisely detecting a change in capacitance by patterns of valleys and ridges of a fingerprint to recognize the fingerprint.

A structure of a capacitive fingerprint sensor module according to the related art generally is a multilayer cored-type general ball grid array (BGA) substrate structure based on a copper clad laminate (CCL). For example, an IC for a sensor and a passive component are surface-mounted on a lower surface of a ball grid array (BGA) substrate on which patterns having a fingerprint recognition sensor function are formed, using low melting point metals, solder balls, or the like, are formed on the same level, and the BGA substrate is then mounted on a mainboard of an electronic device. In such a substrate structure, it is difficult to form fine wirings on Tx and Rx layers and make the Tx and Rx layers ultra-thin, which are important in improving transmitting and receiving sensitivities of a sensor, and it is technically difficult to secure perfect flatness of the outermost layer touched by a fingerprint. In addition, it is necessary to use a ferroelectric insulating material in order to improve efficiency of touch sensing including the Tx and Rx layers, but it is difficult to use a material other than existing substrate materials. In addition, since the IC for a sensor and the passive component are mounted on a lower end portion of the substrate, a thickness of the IC for a sensor and a thickness of the passive component are limited, and a height of the solder balls needs to be large. Further, in recent, customer's needs to easily change an entire thickness of a fingerprint recognition sensor from an ultra-thin type to a thick plate type have increased.

In the fan-out semiconductor package 100A according to the exemplary embodiment, the circuit layers 142 of the connection member 140 including the sensing patterns Tx and Rx may be manufactured by a semiconductor method to enable ultra-fine patterns and thinness of insulating layers, resulting in improvement of transmitting and receiving sensitivities of a sensor. In addition, a thickness of the IC 120 for a sensor may be easily changed depending on desired specifications by controlling a thickness of the core member 110, and an entire thickness of the fan-out semiconductor package 100A may thus be easily controlled. In addition, the IC 120 for a sensor may be disposed in the through-hole 110H of the core member 110, such that a height of electrical connection structures 170 such as solder balls for connecting the fan-out semiconductor package to a mainboard of an electronic device may be reduced. In addition, the wiring layers 112a and 112b may be formed in the core member 110 to further improve a thickness and performance of the fan-out semiconductor package 100A. In addition, since the passive components 190 are disposed side-by-side with the IC 120 for a sensor in the through-hole 110H, a degree of integration of a size may be increased and an electrical connection distance may be decrease to significantly decrease noise.

Meanwhile, the sensing patterns Tx and Rx may include Rx (Reset Transistor) patterns and Tx (Transfer Transistor) patterns formed on different layers M1 and M2. In this case, the Tx patterns and the Rx patterns may be disposed in a mesh form in relation to a projection surface, as illustrated in FIG. 11. In addition, when fine circuit technology is used to form the patterns, the Rx patterns may be formed so that a line width Wr thereof is narrow and an interval Sr therebetween is wide, while the Tx patterns may be formed so that a line width Wt thereof is wide and an interval St therebetween is narrow. Therefore, the Tx patterns may easily transfer a signal recognized through a wide region to the Rx patterns, and the transferred signal may be transferred to other layers M3 and M4 through vias.

Alternatively, the sensing patterns Tx and Rx may include Tx patterns and Rx patterns formed on the same layer M1, as illustrated in FIG. 12. In this case, one layer M2 may be omitted unlike the drawing. That is, the sensing patterns Tx and Rx may be formed on the same layer M1 using fine spacing technology. In this case, the Tx patterns and the Rx patterns may be alternately disposed in a diamond form while having a predetermined interval g therebetween to significantly increase a sensing sensitivity. Individual pads of the Tx patterns may be again connected to each other on a layer M3 below the layer M1 through vias to improve a sensing sensitivity. Pads of the Rx patterns may be connected to each other on the outermost layer M1 through a fine circuit. The Tx patterns and the Rx patterns may be alternately disposed in the diamond form while having a predetermined interval g therebetween. Certain forms of the Tx patterns and the Rx patterns are not particularly limited. For example, corners of the respective patterns may have a round shape unlike the drawing.

Meanwhile, a passivation layer 150 may further be disposed on the connection member 140. In this case, the passivation layer 150 may have a dielectric constant greater than that of each of insulating layers 141 constituting the connection member 140. That is, an insulating material having a high dielectric constant, that is, a ferroelectric insulating material may be used in the passivation layer 150 on which the sensing patterns Tx and Rx are disposed. In this case, the sensing sensitivity may be significantly increased more effectively. In addition, at least one M3 of the circuit layers 142 of the connection member 140 may include electromagnetic wave shielding patterns. The electromagnetic wave shielding patterns may have, for example, a plane shape. The electromagnetic wave shielding patterns may shield electromagnetic waves generated from the IC 120 for a sensor, a layer M4 having routing patterns among the circuit layers 142, or the like. The electromagnetic wave shielding patterns may also shield electromagnetic waves generated from other components depending on a disposition form.

Meanwhile, the encapsulant 130 is controlled to cover the inactive surface of the IC 120 for a sensor, thicknesses tA1 and tA2 of the wiring layers 112a and 112b constituting the core member 110 are controlled, or materials 111as and 111bs of an insulating layer 111 constituting the core member 110 are controlled, such that a warpage problem of the fan-out semiconductor package 100A may be solved even though the fan-out semiconductor package 100A has a subminiature size and an ultra-thin thickness.

In detail, a first wiring layer 112a may be disposed on an upper surface of the insulating layer 111 and be in contact with the connection member 140. A second wiring layer 112b may be disposed on a lower surface of the insulating layer 111, and at least portions of the second wiring layer 112b may be exposed by openings 131 formed in the encapsulant 130. In this case, the thickness tA2 of the second wiring layer 112b may be greater than the thickness tA1 of the first wiring layer 112a. Since the connection member 140 disposed above the IC 120 for a sensor generally has a coefficient of thermal expansion (CTE) value greater than that of the encapsulant 130 disposed below the IC 120 for a sensor, warpage of the fan-out semiconductor package 100A may occur depending on a change in an ambient temperature, and the thinner the encapsulant 130, the larger the warpage of the fan-out semiconductor package 100A. Since it is advantageous to decrease a thickness of the encapsulant 130 in order to decrease an entire thickness of the fan-out semiconductor package 100A, the warpage of the fan-out semiconductor package 100A needs to be controlled by another method. In this case, when the thickness tA2 of the second wiring layer 112b adjacent to the encapsulant 130 is made to be greater than the thickness tA1 of the first wiring layer 112a adjacent to the connection member 140, a difference between the CTEs described above may be corrected to some degrees, and the warpage of the fan-out semiconductor package 100A may thus be controlled.

In addition, a material of the insulating layer 111 may be a prepreg 111*as* including a first resin layer 111*a*1 including a thermoplastic resin or a thermosetting resin, a second resin layer 111*a*2 including the same material as that of the first resin layer 111*a*1, and a reinforcing material lilac such as a glass fiber (or a glass cloth or a glass fabric), or the like, disposed between the first resin layer 111*a*1 and the second resin layer 111*a*2, as illustrated in FIG. 13. In this case, a thickness ta2 of the second resin layer 111*a*2 disposed adjacent to the encapsulant 130 is made to be greater than a thickness ta1 of the first resin layer 111*a*1 disposed adjacent to the connection member 140, such that the difference between the CTEs described above may be corrected to some degrees, and the warpage of the fan-out semiconductor package 100A may thus be controlled. Meanwhile, the first and second resin layers 111*a*1 and 111*a*2 may include inorganic fillers such as silica, or the like, and the CTEs may also be controlled by controlling amounts of the inorganic fillers.

Alternatively, a material of the insulating layer 111 may be a prepreg 111*bs* including a first resin layer 111*b*1 including a thermoplastic resin or a thermosetting resin, a second resin layer 111*b*2 including a material having physical properties different from as those of the material of the first resin layer 111*b*1, and a reinforcing material 111*bc* such as a glass fiber (or a glass cloth or a glass fabric), or the like, disposed between the first resin layer 111*b*1 and the second resin layer 111*b*2, as illustrated in FIG. 14. In this case, when a material of which a CTE and an elastic modulus are relatively high is used as a material of the second resin layer 111*b*2 disposed adjacent to the encapsulant 130 and a material of which a CTE and an elastic modulus are relatively low is used as a material of the first resin layer 111*b*1 disposed adjacent to the connection member 140, the difference between the CTEs described above may be corrected to some degrees, and the warpage of the fan-out semiconductor package 100A may thus be controlled. Thicknesses tb1 and tb2 of the first resin layer 111*b*1 and the second resin layer 111*b*2 may be the same as each other or be different from each other. Meanwhile, the first and second resin layers 111*b*1 and 111*b*2 may include inorganic fillers such as silica, or the like, and the CTEs may also be controlled by controlling amounts of the inorganic fillers.

The respective components included in the fan-out semiconductor package 100A according to the exemplary embodiment will hereinafter be described in more detail.

The core member 110 may maintain rigidity of the fan-out semiconductor package 100A, and serve to secure uniformity of a thickness of the encapsulant 130. The IC 120 for a sensor and the passive components 190 may be electrically connected to the mainboard of the electronic device through the connection member 140, the electrical connection structures 170, and the like, by the core member 110. The core member 110 may include the plurality of wiring layers 112*a* and 112*b* to effectively redistribute the connection pads 122 of the IC 120 for a sensor, and may provide a wide wiring design region to suppress circuit layers from being formed in other regions. The IC 120 for a sensor and the passive components 190 may be disposed side-by-side with each other in the through-hole 110H to be spaced apart from the core member 110 by a predetermined distance. Side surfaces of the IC 120 for a sensor and the passive components 190 may be surrounded by the core member 110. The passive components 190 may be disposed in the through-hole 110H in which the IC 120 for a sensor is disposed, but may also be disposed in a separately formed through-hole, if necessary.

A material of the insulating layer 111 may be a general insulating material. For example, a thermosetting resin such as an epoxy resin, a thermoplastic resin such as a polyimide resin, or a resin including an inorganic filler such as silica, alumina, or the like, more specifically, Ajinomoto Build up Film (ABF), FR-4, Bismaleimide Triazine (BT), a photoimagable dielectric (PID) resin, or the like, may be used. Alternatively, a material in which a thermosetting resin or a thermoplastic resin is impregnated together with an inorganic filler in a reinforcing material such as a glass fiber (or a glass cloth or a glass fabric), for example, prepreg, or the like, may also be used.

Meanwhile, the material of the insulating layer 111 may be the prepreg 111*as* including the first resin layer 111*a*1 including the thermoplastic resin or the thermosetting resin, the second resin layer 111*a*2 including the same material as that of the first resin layer 111*a*1, and the reinforcing material lilac such as the glass fiber (or the glass cloth or the glass fabric), or the like, disposed between the first resin layer 111*a*1 and the second resin layer 111*a*2, as described above. In this case, the thickness ta2 of the second resin layer 111*a*2 disposed adjacent to the encapsulant 130 is made to be greater than the thickness ta1 of the first resin layer 111*a*1 disposed adjacent to the connection member 140, such that the difference between the CTEs described above may be corrected to some degrees, and the warpage of the fan-out semiconductor package 100A may thus be controlled. The first and second resin layers 111*a*1 and 111*a*2 may include the inorganic fillers such as the silica, or the like, and the CTEs may also be controlled by controlling the amounts of the inorganic fillers.

Alternatively, the material of the insulating layer 111 may be the prepreg 111*bs* including the first resin layer 111*b*1 including the thermoplastic resin or the thermosetting resin, the second resin layer 111*b*2 including the material having the physical properties different from as those of the material of the first resin layer 111*b*1, and the reinforcing material 111*bc* such as the glass fiber (or the glass cloth or the glass fabric), or the like, disposed between the first resin layer 111*b*1 and the second resin layer 111*b*2, as described above. In this case, when the material of which the CTE and the elastic modulus are relatively high is used as the material of the second resin layer 111*b*2 disposed adjacent to the encapsulant 130 and the material of which the CTE and the elastic modulus are relatively low is used as the material of the first resin layer 111*b*1 disposed adjacent to the connection member 140, the difference between the CTEs described above may be corrected to some degrees, and the warpage of the fan-out semiconductor package 100A may thus be controlled. The thicknesses tb1 and tb2 of the first resin layer 111*b*1 and the second resin layer 111*b*2 may be the same as each other or be different from each other. The first and second resin layers 111*b*1 and 111*b*2 may include the inorganic fillers such as the silica, or the like, and the CTEs may also be controlled by controlling the amounts of the inorganic fillers.

The wiring layers 112*a* and 112*b* may include a conductive material such as copper (Cu), aluminum (Al), silver (Ag), tin (Sn), gold (Au), nickel (Ni), lead (Pb), titanium (Ti), or alloys thereof. The wiring layers 112*a* and 112*b* may perform various functions depending on designs of corresponding layers. For example, the wiring layers 112*a* and 112*b* may include ground (GND) patterns, power (PWR) patterns, signal (S) patterns, and the like. Here, the signal (S) patterns may include various signals except for the ground (GND) patterns, the power (PWR) patterns, and the like, such as data signals, and the like. In addition, the wiring layers 112*a* and 112*b* may include pad patterns for vias, pad patterns for electrical connection structures, and the like.

Meanwhile, the first wiring layer 112*a* may be disposed on the upper surface of the insulating layer 111 and be in contact with the connection member 140. The second wiring layer 112*b* may be disposed on the lower surface of the insulating layer 111, and at least portions of the second wiring layer 112*b* may be exposed by the openings 131 formed in the encapsulant 130. In this case, the thickness tA2 of the second wiring layer 112*b* may be greater than the thickness tA1 of the first wiring layer 112*a*. That is, since it is advantageous to decrease the thickness of the encapsulant 130 in order to decrease the entire thickness of the fan-out semiconductor package 100A, the warpage of the fan-out semiconductor package 100A needs to be controlled by another method. In this case, when the thickness tA2 of the second wiring layer 112*b* adjacent to the encapsulant 130 is made to be greater than the thickness tA1 of the first wiring layer 112*a* adjacent to the connection member 140, the difference between the CTEs described above may be corrected to some degrees, and the warpage of the fan-out semiconductor package 100A may thus be controlled.

A thickness of each of the wiring layers 112*a* and 112*b* may be greater than that of each of the circuit layers 142. The core member 110 may have a thickness equal to or greater than that of the IC 120 for a sensor and may be manufactured by a substrate process, and the wiring layers 112*a* and 112*b* may also be formed to have larger sizes. On the other hand, the circuit layers 142 of the connection member 140 may be manufactured by a semiconductor process for thinness, and may thus be formed to have relatively smaller sizes.

A material of each of the vias 113 may be a conductive material such as copper (Cu), aluminum (Al), silver (Ag), tin (Sn), gold (Au), nickel (Ni), lead (Pb), titanium (Ti), or alloys thereof. Each of the vias 113 may be completely filled with the conductive material, or the conductive material may be formed along a wall of each of via holes. Each of the vias 113 may have a hourglass shape, but is not limited thereto. The first and second wiring layers 112*a* and 112*b* may be electrically connected to each other through the vias 113, and upper and lower portions of the fan-out semiconductor package 100A may be electrically connected to each other through the vias 113.

The IC 120 for a sensor may be an integrated circuit (IC) provided in an amount of several hundred to several million or more elements integrated in a single chip. The IC for a sensor may be, for example, an application specific integrated circuit (ASIC) capable of performing fingerprint recognition sensor processing, but is not limited thereto. The IC 120 for a sensor may be formed on the basis of an active wafer. In this case, a base material of a body 121 of the IC 120 for a sensor may be silicon (Si), germanium (Ge), gallium arsenide (GaAs), or the like. Various circuits may be formed on the body 121. The connection pads 122 may electrically connect the IC 120 for a sensor to other components. A material of each of the connection pads 122 may be a conductive material such as aluminum (Al), or the like. A passivation layer 123 exposing the connection pads 122 may be formed on the body 121, and may be an oxide film, a nitride film, or the like, or a double layer of an oxide layer and a nitride layer. A lower surface of the connection pad 122 may have a step with respect to a lower surface of the encapsulant 130 through the passivation layer 123. Resultantly, a phenomenon in which the encapsulant 130 bleeds into the lower surface of the connection pads 122 may be prevented to some extent. An insulating layer (not illustrated), and the like, may also be further disposed in other required positions. The connection pads 122 of the IC 120 for a sensor may be in physical contact with vias 143 of the connection member 140. That is, the connection member 140 may be directly formed on the IC 120 for a sensor.

The passive components 190 may be any known passive components such as capacitors, inductors, beads, or the like. The number of passive components 190 is not particularly limited, but may be more than that illustrated in the drawings or be less than that illustrated in the drawings, and the passive components 190 may be the same as or different from each other. The passive components 190 may include the external electrodes 190P, and each of the external electrodes 190 may be formed of copper (Cu), aluminum (Al), and/or silver (Ag). That is, the passive components 190 are not surface-mounted on the connection member 140 by surface mounting technology, and the connection member 140 may be directly formed on the passive components 190. In this case, the vias 143 of the connection member 140 may be in physical contact with the external electrodes 190P. Therefore, each of the external electrodes 190P may be formed of a general metal such as copper (Cu), aluminum (Al), and/or silver (Ag) rather than tin (Sn), or the like, unlike a surface mounting type passive component.

The encapsulant 130 may protect the IC 120 for a sensor, the passive components 190, and the like. An encapsulation form of the encapsulant 130 is not particularly limited, but may be a form in which the encapsulant 130 surrounds at least portions of the IC 120 for a sensor and the passive components 190. For example, the encapsulant 130 may cover at least portions of the core member 110, the inactive surface of the IC 120 for a sensor, and the passive components 190 and fill at least portions of the through-hole 110H. In addition, the encapsulant 130 may also fill at least a portion of a space between the passivation layer 123 of the IC 120 for a sensor and the connection member 140. Certain materials of the encapsulant 130 are not particularly limited. For example, an insulating material may be used as the certain materials of the encapsulant 130. In this case, the insulating material may be a thermosetting resin such as an epoxy resin, a thermoplastic resin such as polyimide, a resin having a reinforcing material such as an inorganic filler impregnated in the thermosetting resin and the thermoplastic resin, for example, ABF, FR-4, BT, a PID resin, or the like. In addition, any known molding material such as an EMC, or the like, may also be used. Alternatively, a resin in which a thermosetting resin or a thermoplastic resin is impregnated together with an inorganic filler in a core material such as a glass fiber (or a glass cloth or a glass fabric) may also be used as the insulating material. Alternatively, a photoimagable encapsulant (PIE) may also be used as the insulating material.

The connection member 140 may redistribute the connection pads 122 of the IC 120 for a sensor, and may include the circuit layers 142 capable of implementing a high sensitivity fingerprint recognition function. Several tens to several hundreds of connection pads 122 having various functions may be redistributed by the connection member 140, and may be physically or electrically externally connected through the electrical connection structures 170 depending on the functions. In addition, a fingerprint recognition function that is to implement the high sensitivity fingerprint recognition function may be implemented. The connection member 140 may include the insulating layers 141, the circuit layers 142 disposed on the insulating layers 141, and the vias 143 penetrating through the insulating layers 141 and connected to the circuit layers 142.

For example, an insulating material may be used as a material of each of the insulating layers 141. In this case, the insulating material may be a thermosetting resin such as an epoxy resin, a thermoplastic resin such as a polyimide resin, a resin having a reinforcing material such as an inorganic filler impregnated in the thermosetting resin and the thermoplastic resin, for example, ABF, FR-4, BT, a PID resin, or the like. It may be advantageous in forming fine patterns that a photosensitive insulating material such as a PID resin is used as the material of the insulating layer. When the insulating layers 141 are multiple layers, materials of the insulating layers 141 may be the same as each other, and may also be different from each other, if necessary. When the insulating layers 141 are the multiple layers, the insulating layers 141 may be integrated with each other depending on a process, such that a boundary therebetween may also not be apparent.

The circuit layers 142 may include the layers M1 and M2 capable of performing a fingerprint recognition function, the layer M3 capable of performing a shield function, and the layer M4 capable of performing a redistribution function. A material of each of the circuit layers 142 may be a conductive material such as copper (Cu), aluminum (Al), silver (Ag), tin (Sn), gold (Au), nickel (Ni), lead (Pb), titanium (Ti), or alloys thereof. The circuit layers 142 may perform various functions depending on designs of corresponding layers. For example, the layer M1 and the layer M2 may include the Rx patterns and the Tx patterns. The layer M3 may include the electromagnetic wave shielding patterns. The layer M4 may include ground (GND) patterns, power (PWR) patterns, signal (S) patterns, and the like. Here, the signal (S) patterns may include various signals except for the ground (GND) patterns, the power (PWR) patterns, and the like, such as data signals, and the like. In addition, these layers M1 to M4 may include various kinds of pad patterns. The layer M3 capable of performing the shield function may be omitted. In this case, an insulating layer, most adjacent to the IC 120 for a sensor, of the insulating layers 141 of the connection member 140 may have a thickness greater than those of the other insulating layers. The shield function may be performed through such a thickness difference, and the circuit layers may thus be thinned. The layers M1 to M4 may be disposed to become sequentially closer to the active surface of the IC 120 for a sensor. That is, the layer M4 may be closest to the active surface of the IC 120 for a sensor, and the layer M1 may be most distance from the IC 120 for a sensor.

The vias 143 may electrically connect the connection pads 122, the circuit layers 142, and the like, formed on different layers to each other, resulting in an electrical path in the fan-out semiconductor package 100A. A material of each of the vias 143 may be a conductive material such as copper (Cu), aluminum (Al), silver (Ag), tin (Sn), gold (Au), nickel (Ni), lead (Pb), titanium (Ti), or alloys thereof. Each of the vias 143 may be completely filled with the conductive material, or the conductive material may also be formed along a wall of each of the vias. In addition, each of the vias 143 may have any shape known in the related art, such as a tapered shape, a cylindrical shape, and the like.

The passivation layer 150 may protect the connection member 140 from external physical or chemical damage. The passivation layer 150 may be the outermost layer touched by a fingerprint. A material of the passivation layer 150 is not particularly limited, but may be any known insulating material. However, a ferroelectric insulating material may be used as the material of the passivation layer 150 in order to improve efficiency of touch sensing. For example, a dielectric constant of the passivation layer 150 may be greater than that of the insulating layer 141 of the connection member 140.

The electrical connection structures 170 may be additionally configured to physically or electrically externally connect the fan-out semiconductor package 100A. For example, the fan-out semiconductor package 100A may be mounted on the mainboard of the electronic device through the electrical connection structures 170. Each of the electrical connection structures 170 may be formed of a low melting point metal, for example, a solder such as tin (Sn)-aluminum (Al)-copper (Cu) alloys, or the like. However, this is only an example, and a material of each of the electrical connection structures 170 is not particularly limited thereto. Each of the electrical connection structures 170 may be a land, a ball, a pin, or the like. The electrical connection structures 170 may be formed as a multilayer or single layer structure. When the electrical connection structures 170 are formed as a multilayer structure, the electrical connection structures 170 may include a copper (Cu) pillar and a solder. When the electrical connection structures 170 are formed as a single layer structure, the electrical connection structures 170 may include a tin-silver solder or copper (Cu). However, this is only an example, and the electrical connection structures 170 are not limited thereto.

The number, an interval, a disposition form, and the like, of electrical connection structures 170 are not particularly limited, but may be sufficiently modified depending on design particulars by those skilled in the art. For example, the electrical connection structures 170 may be provided in an amount of several tens to several thousands according to the number of connection pads 122 of the IC 120 for a sensor, or may be provided in an amount of several tens to several thousands or more or several tens to several thousands or less. The electrical connection structures 170 may be connected to the second wiring layer 112b exposed through the openings 131 of the encapsulant 130 via under-bump metal layers (not illustrated), if necessary. A surface treatment layer (not illustrated) may be formed on a surface of the exposed second wiring layer 112b.

At least one of the electrical connection structures 170 may be disposed in a fan-out region. The fan-out region refers to a region except for the region in which the IC 120 for a sensor is disposed. That is, the fan-out semiconductor package 100A according to the exemplary embodiment may be a fan-out package. The fan-out package may have excellent reliability as compared to a fan-in package, may implement a plurality of input/output (I/O) terminals, and may facilitate a 3D interconnection. In addition, as compared to a ball grid array (BGA) package, a land grid array (LGA) package, or the like, the fan-out package may be mounted on an electronic device without a separate board. Thus, the fan-out package may be manufactured to have a small thickness, and may have price competitiveness.

Meanwhile, although not illustrated in the drawings, a metal layer may further be disposed on the wall of the through-hole 110H, if necessary. The metal layer may serve to effectively dissipate heat generated from the IC 120 for a sensor. In addition, the metal layer may also serve to shield electromagnetic waves. In addition, the number of through-holes 110H may be plural and ICs 120 for a sensor or passive components may be disposed in the through-holes 110H, respectively. In addition to the structures described above, any structures known in the related art may be applied.

Figure 15:
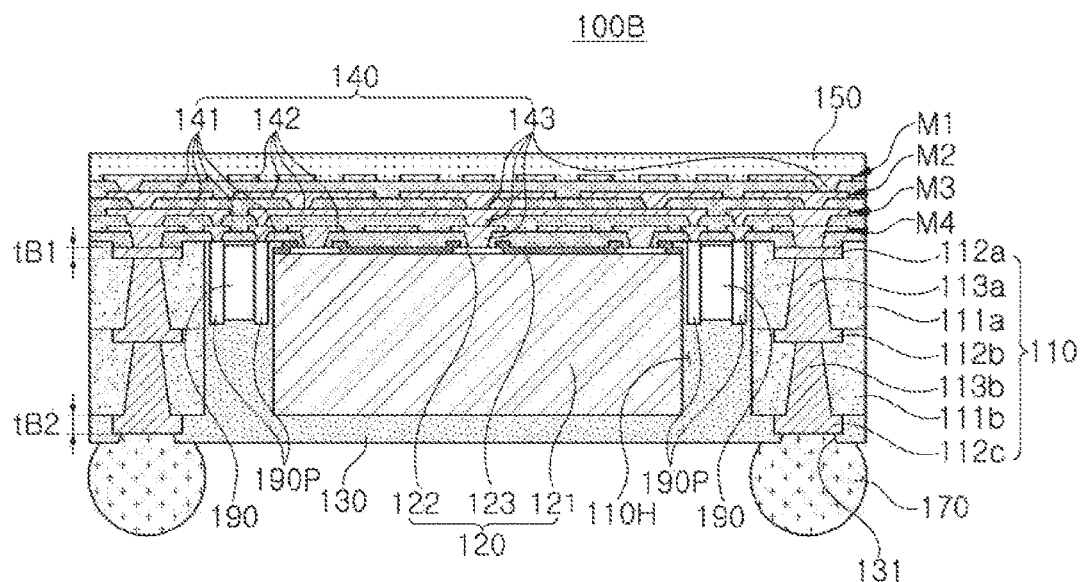
FIG. 15 is a schematic cross-sectional view illustrating another example of a fan-out semiconductor package.

FIG. 15 is a schematic cross-sectional view illustrating another example of a fan-out semiconductor package.

A core member 110 may include a first insulating layer 111a, a first wiring layer 112a embedded in the first insulating layer 111a so that one surface thereof is exposed and in contact with a connection member 140, a second wiring layer 112b disposed on the other surface of the first insulating layer 111a opposing one surface of the first insulating layer 111a in which the first wiring layer 112a is embedded, a second insulating layer 111b disposed on the first insulating layer 111a and covering the second wiring layer 112b, and a third wiring layer 112c disposed on the second insulating layer 111b. The first and second wiring layers 112a and 112b and the second and third wiring layers 112b and 112c may be electrically connected to each other through first and second vias 113a and 113b penetrating through the first and second insulating layers 111a and 111b, respectively. At least one of the first insulating layer 111a or the second insulating layer 111b, or both, may be made of the above-described material 111as or the above-described material 111bs. In a case in which the material 111as is used, the first resin layer 111a1 thereof may be closer to the connection member 140 than the second resin layer 111a2 thereof. In a case in which the material 111bs is used, the first resin layer 111b1 thereof may be closer to the connection member 140 than the second resin layer 111b2 thereof. An overlapped description will be omitted to avoid redundancy.

Since the first wiring layer 112a is embedded in the first insulating layer 111a, an insulating distance of an insulating layer 141 of the connection member 140 may be substantially constant. Since the core member 110 may include a large number of wiring layers 112a, 112b, and 112c, the connection member 140 may further be simplified. Therefore, a decrease in a yield depending on a defect occurring in a process of forming the connection member 140 may be suppressed, and the connection member 140 may be thinned. The first wiring layer 112a may be recessed into the first insulating layer 111a, such that an upper surface of the first insulating layer 111a and an upper surface of the first wiring layer 112a have a step therebetween. Resultantly, when an encapsulant 130 is formed, a phenomenon in which a material of the encapsulant 130 bleeds to pollute the first wiring layer 112a may be prevented.

The upper surface of the first wiring layer 112a of the core member 110 may be disposed on a level below an upper surface of a connection pad 122 of an IC 120 for a sensor. In addition, a distance between a circuit layer 142 of the connection member 140 and the first wiring layer 112a of the core member 110 may be greater than that between the circuit layer 142 of the connection member 140 and the connection pad 122 of the IC 120 for a sensor. The reason is that the first wiring layer 112a may be recessed into the first insulating layer 111a. The second wiring layer 112b of the core member 110 may be disposed on a level between an active surface and an inactive surface of the IC 120 for a sensor. The core member 110 may be formed at a thickness corresponding to that of the IC 120 for a sensor. Therefore, the second wiring layer 112b formed in the core member 110 may be disposed on the level between the active surface and the inactive surface of the IC 120 for a sensor.

Thicknesses of the wiring layers 112a, 112b, and 112c of the core member 110 may be greater than those of the circuit layers 142 of the connection member 140. The first wiring layer 112a may be in contact with the connection member 140. The third wiring layer 112c may have portions exposed by openings 131 formed in the encapsulant 130. In this case, a thickness tB2 of the third wiring layer 112c may be greater than a thickness tB1 of the first wiring layer 112a. Among the first to third wiring layers 112a, 112b, and 112c, the thickness tB2 of the third wiring layer 112c may be the greatest. When the thickness tB2 of the third wiring layer 112c adjacent to the encapsulant 130 is made to be greater than the thickness tB1 of the first wiring layer 112a adjacent to the connection member 140 or to be the greatest among the first to third wiring layers 112a, 112b, and 112c, a difference between the CTEs described above may be corrected to some degrees, and the warpage of the fan-out semiconductor package 100B may thus be controlled. The core member 110 may have a thickness equal to or greater than that of the IC 120 for a sensor and may be manufactured by a substrate process, and the wiring layers 112a, 112b, and 112c may also be formed to have larger sizes. On the other hand, the circuit layers 142 of the connection member 140 formed through a fine circuit process such as a semiconductor process may be formed to have a relatively small size for thinness.

Figure 16:
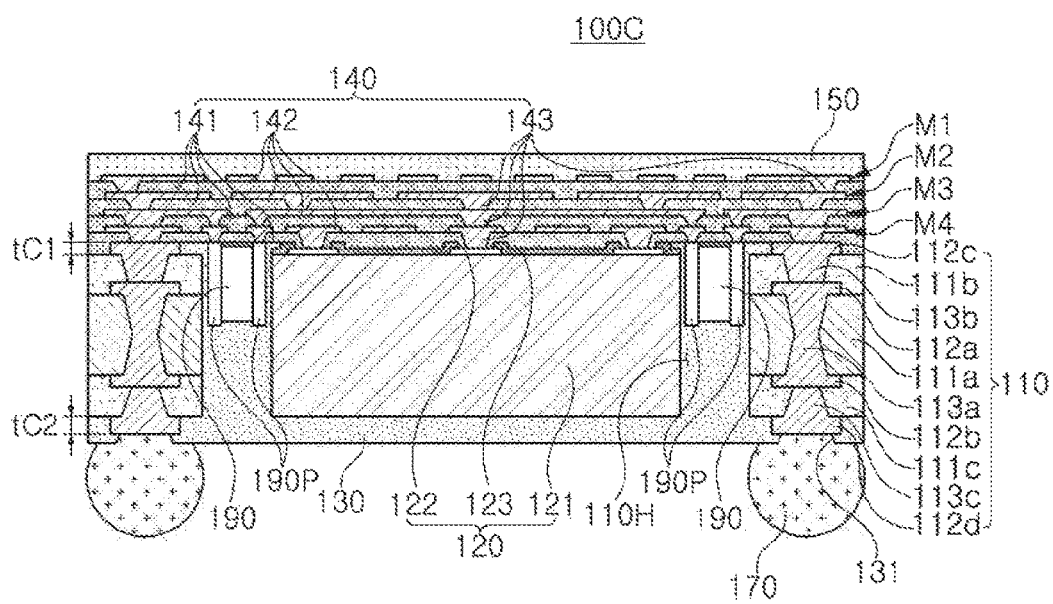
FIG. 16 is a schematic cross-sectional view illustrating another example of a fan-out semiconductor package.

FIG. 16 is a schematic cross-sectional view illustrating another example of a fan-out semiconductor package.

Referring to the drawing, in a fan-out semiconductor package 100C according to another exemplary embodiment in the present disclosure, a core member 110 may include a first insulating layer 111a, a first wiring layer 112a and a second wiring layer 112b disposed on opposite surfaces of the first insulating layer 111a, respectively, a second insulating layer 111b disposed on the first insulating layer 111a and covering the first wiring layer 112a, a third wiring layer 112c disposed on the second insulating layer 111b, a third insulating layer 111c disposed on the first insulating layer 111a and covering the second wiring layer 112b, and a fourth wiring layer 112d disposed on the third insulating layer 111c. Since the core member 110 may include a large number of wiring layers 112a, 112b, 112c, and 112d, a connection member 140 may further be simplified. The first to fourth wiring layers 112a, 112b, 112c, and 112d may be electrically connected to each other through first to third vias 113a, 113b, and 113c penetrating through the first to third insulating layers 111a, 111b, and 111c, respectively.

The first insulating layer 111a may have a thickness greater than those of the second insulating layer 111b and the third insulating layer 111c. The first insulating layer 111a may be basically relatively thick in order to maintain rigidity, and the second insulating layer 111b and the third insulating layer 111c may be introduced in order to form a larger number of wiring layers 112c and 112d. The first insulating layer 111a may include an insulating material different from those of the second insulating layer 111b and the third insulating layer 111c. For example, the first insulating layer 111a may be, for example, prepreg including a core material, an inorganic filler, and an insulating resin, and the second insulating layer 111b and the third insulating layer 111c may be an ABF or a photosensitive insulating film including an inorganic filler and an insulating resin. The first insulating layer 111a may be made of the above-described material 111as or the above-described material 111bs. In a case in which the material 111as is used to form the first insulating layer 111a, the first resin layer 111a1 may be closer to the connection member 140 than the second resin layer 111a2. In a case in which the material 111bs is used to form the first insulating layer 111a, the first resin layer 111b1 may be closer to the connection member 140 than the second resin layer 111b2. An overlapped description will be omitted to avoid redundancy. However, the materials of the first insulating layer 111a and the second and third insulating layers 111b and 111c are not limited thereto. Similarly, the first via 113a may have a diameter greater than those of the second via 113b and the third via 113c.

An upper surface of the third wiring layer 112c of the core member 110 may be disposed on a level above an upper surface of a connection pad 122 of an IC 120 for a sensor. In addition, a distance between a circuit layer 142 of the connection member 140 and the third wiring layer 112c of the core member 110 may be smaller than that between the circuit layer 142 of the connection member 140 and the connection pad 122 of the IC 120 for a sensor. The reason is that the third wiring layer 112c may be disposed on the second insulating layer 111b in a protruding form, resulting in being contact with the connection member 140. The first wiring layer 112a and the second wiring layer 112b of the core member 110 may be disposed on a level between an active surface and an inactive surface of the IC 120 for a sensor. The core member 110 may be formed at a thickness corresponding to that of the IC 120 for a sensor. Therefore, the first wiring layer 112a and the second wiring layer 112b formed in the core member 110 may be disposed on the level between the active surface and the inactive surface of the IC 120 for a sensor.

Thicknesses of the wiring layers 112a, 112b, 112c, and 112d of the core member 110 may be greater than those of the circuit layers 142 of the connection member 140. The third wiring layer 112c may be in contact with the connection member 140. The fourth wiring layer 112d may have portions exposed by openings 131 formed in the encapsulant 130. In this case, a thickness tC2 of the fourth wiring layer 112d may be greater than a thickness tC1 of the third wiring layer 112c. Among the first to fourth wiring layers 112a, 112b, 112c, and 112d, the thickness tC2 of the fourth wiring layer 112d may be the greatest. In this case, when the thickness tC2 of the fourth wiring layer 112d adjacent to the encapsulant 130 is made to be greater than the thickness tC1 of the third wiring layer 112c adjacent to the connection member 140 or to be the greatest among the first to fourth wiring layers 112a, 112b, 112c, and 112d, a difference between the CTEs described above may be corrected to some degrees, and the warpage of the fan-out semiconductor package 100C may thus be controlled. The core member 110 may have a thickness equal to or greater than that of the IC 120 for a sensor and may be manufactured by a substrate process, and the wiring layers 112a, 112b, 112c, and 112d may also be formed to have larger sizes. On the other hand, the circuit layers 142 of the connection member 140 may be manufactured by a semiconductor process for thinness, and may thus be formed to have relatively smaller sizes. A description of other configurations overlaps that described above, and is thus omitted.

As set forth above, according to the exemplary embodiments in the present disclosure, a subminiature and ultra-thin fan-out sensor package having an excellent fingerprint recognition function, a high degree of integration, and excellent rigidity may be provided.

While exemplary embodiments have been shown and described above, it will be apparent to those skilled in the art that modifications and variations could be made without departing from the scope of the present invention as defined by the appended claims.

What is claimed is:

1. A fan-out sensor package comprising:
a core member including a wiring layer including a plurality of layers and having a through-hole;
an integrated circuit (IC) for a sensor disposed in the through-hole and having an active surface having connection pads disposed thereon and an inactive surface opposing the active surface;
a passive component disposed side-by-side with the IC for the sensor disposed in the through-hole and having external electrodes;
an encapsulant covering at least portions of the core member, the inactive surface of the IC for the sensor disposed in the through-hole, and the passive component and filling at least portions of the through-hole; and
a connection member disposed on the core member, the active surface of the IC for the sensor disposed in the through-hole, and the passive component and including a circuit layer including a plurality of layers,
wherein the circuit layer is electrically connected to the wiring layer, the connection pads, and the external electrodes, and
the circuit layer includes sensing patterns detecting a change in capacitance.

2. The fan-out sensor package of claim 1, wherein the core member includes an insulating layer, a first wiring layer disposed on a first surface of the insulating layer and in contact with the connection member, a second wiring layer disposed on a second surface of the insulating layer opposing the first surface of the insulating layer and at least partially exposed by openings formed in the encapsulant, and vias penetrating through the insulating layer and electrically connecting the first and second wiring layers to each other.

3. The fan-out sensor package of claim 2, wherein the second wiring layer has a thickness greater than that of the first wiring layer.

4. The fan-out sensor package of claim 2, wherein the insulating layer includes first and second resin layers and a reinforcing material disposed between the first and second resin layers,
a distance between the first resin layer and the connection member is smaller than that between the second resin layer and the connection member, and
the reinforcing material includes a glass fiber.

5. The fan-out sensor package of claim 4, wherein the second resin layer has a thickness greater than that of the first resin layer.

6. The fan-out sensor package of claim 4, wherein the second resin layer has a coefficient of thermal expansion (CTE) and an elastic modulus greater than those of the first resin layer.

7. The fan-out sensor package of claim 2, further comprising electrical connection structures disposed in the openings of the encapsulant and electrically connected to the second wiring layer exposed through the openings of the encapsulant.

8. The fan-out sensor package of claim 1, wherein the wiring layer has a thickness greater than that each of the plurality of layers of the circuit layer.

9. The fan-out sensor package of claim 1, wherein the connection member includes vias electrically connecting the circuit layer to the wiring layer, the connection pads, and the external electrodes, and
the connection pads and the external electrodes are in direct contact with the vias.

10. The fan-out sensor package of claim 9, wherein the external electrodes includes at least one metal selected from the group consisting of copper (Cu), aluminum (Al), and silver (Ag).

11. The fan-out sensor package of claim 1, wherein the sensing patterns include transmit (Tx) and receive (Rx)

patterns disposed on different circuit layers, and the Tx and Rx patterns are disposed in a mesh form in relation to a projection surface.

12. The fan-out sensor package of claim 11, wherein a line width of the TX patterns is greater than that of the Rx patterns, and
an interval between the TX patterns is smaller than that between the Rx patterns.

13. The fan-out sensor package of claim 11, wherein the circuit layer includes a first circuit layer on which the Rx patterns are disposed, a second circuit layer on which the Tx patterns are disposed, a third circuit layer including electromagnetic wave shielding patterns, and a fourth circuit layer including redistribution patterns, and
the first to fourth circuit layers become sequentially closer to the active surface of the IC for the sensor disposed in the through-hole.

14. The fan-out sensor package of claim 1, wherein the sensing patterns include Tx and Rx patterns disposed on the same one of the plurality of layers of the circuit layer, and
the Tx and Rx patterns are alternately disposed in a diamond form.

15. The fan-out sensor package of claim 14, wherein the circuit layer includes a first circuit layer on which the Rx and Tx patterns are formed, a second circuit layer including electromagnetic wave shielding patterns, and a third circuit layer including redistribution patterns, and
the first to third circuit layers become sequentially closer to the active surface of the IC for the sensor disposed in the through-hole.

16. The fan-out sensor package of claim 1, further comprising a passivation layer disposed on the connection member,
wherein the passivation layer has a dielectric constant greater than that of an insulating layer constituting the connection member.

17. The fan-out sensor package of claim 1, wherein the core member includes a first insulating layer, a first wiring layer embedded in the first insulating layer so that one surface thereof is exposed and in contact with the connection member, a second wiring layer disposed on the other surface of the first insulating layer opposing one surface of the first insulating layer in which the first wiring layer is embedded, a second insulating layer disposed on the first insulating layer and covering the second wiring layer, a third wiring layer disposed on the second insulating layer, first vias penetrating through the first insulating layer and electrically connecting the first and second wiring layers to each other, and second vias penetrating through the second insulating layer and electrically connecting the second and third wiring layers to each other.

18. The fan-out sensor package of claim 17, wherein a thickness of the third wiring layer is greater than that of the first wiring layer.

19. The fan-out sensor package of claim 1, wherein the core member includes a first insulating layer, a first wiring layer and a second wiring layer disposed on opposite surfaces of the first insulating layer, respectively, a second insulating layer disposed on the first insulating layer and covering the first wiring layer, a third wiring layer disposed on the second insulating layer and in contact with the connection member, a third insulating layer disposed on the first insulating layer and covering the second wiring layer, a fourth wiring layer disposed on the third insulating layer, first vias penetrating through the first insulating layer and electrically connecting the first and second wiring layers to each other, second vias penetrating through the second insulating layer and electrically connecting the first and third wiring layers to each other, and third vias penetrating through the third insulating layer and electrically connecting the second and fourth wiring layers to each other.

20. The fan-out sensor package of claim 19, wherein a thickness of the fourth wiring layer is greater than that of the third wiring layer.

21. A fan-out sensor package comprising:
a core member including an insulating layer, a first wiring layer disposed on an upper surface of the insulating layer, a second wiring layer disposed on a lower surface of the insulating layer, and vias penetrating through the insulating layer and electrically connecting the first and second wiring layers to each other and having a through-hole;
an IC for a sensor disposed in the through-hole;
an encapsulant covering at least portions of the core member and a lower surface of the IC for the sensor disposed in the through-hole and filling at least portions of the through-hole; and
a connection member disposed on the core member and an upper surface of the IC for the sensor disposed in the through-hole and including a plurality of conductive layers,
wherein the first wiring layer and the connection member face each other, and the second wiring layer has a thickness greater than that of the first wiring layer.

22. The fan-out sensor package of claim 21, further comprising a passive component disposed side-by-side with the IC for the sensor disposed in the through-hole,
wherein at least portions of the passive component are covered with the encapsulant.

* * * * *